(12) United States Patent
Katcha et al.

(10) Patent No.: US 6,975,698 B2
(45) Date of Patent: Dec. 13, 2005

(54) X-RAY GENERATOR AND SLIP RING FOR A CT SYSTEM

(75) Inventors: Jason S. Katcha, Waukesha, WI (US); Jonathan R. Schmidt, Wales, WI (US)

(73) Assignee: General Electric Company, Milwaukee, WI (US)

( * ) Notice: Subject to any disclaimer, the term of this patent is extended or adjusted under 35 U.S.C. 154(b) by 116 days.

(21) Appl. No.: 10/604,192

(22) Filed: Jun. 30, 2003

(65) Prior Publication Data

US 2004/0264642 A1    Dec. 30, 2004

(51) Int. Cl.$^7$ ............................................. H05G 1/10
(52) U.S. Cl. ........................ 378/15; 378/91; 378/101; 378/107
(58) Field of Search ............................. 378/4, 15, 91, 378/101, 104, 107, 193, 196, 197

(56) References Cited

U.S. PATENT DOCUMENTS

| | | | |
|---|---|---|---|
| 4,672,528 A | | 6/1987 | Park et al. ................... 363/98 |
| 4,912,735 A | * | 3/1990 | Beer ............................ 378/15 |
| 4,969,171 A | * | 11/1990 | Yamada et al. ............. 378/101 |
| 4,995,069 A | * | 2/1991 | Tanaka ........................ 378/200 |
| 5,023,768 A | * | 6/1991 | Collier ........................ 363/68 |
| 5,400,385 A | * | 3/1995 | Blake et al. ................. 378/110 |
| 5,451,878 A | | 9/1995 | Wirth et al. ................. 324/322 |
| 5,608,771 A | * | 3/1997 | Steigerwald et al. .......... 378/15 |
| 5,646,835 A | | 7/1997 | Katcha ........................ 363/98 |
| 6,563,717 B2 | * | 5/2003 | Lunding et al. ............. 363/15 |
| 6,674,836 B2 | * | 1/2004 | Harada et al. .............. 378/107 |

OTHER PUBLICATIONS

Steigerwald, Robert L., High-Frequency Resonant Transistor DC-DC Converters, IEEE Transactions on Industrial Electronics, vol. IE-31, No. 2, 1984, pp. 181-191.
Kazimierczuk, M. et al., Resonant Power Converters, Apr. 1995, pp. 149-198, Wiley-Interscience.

* cited by examiner

*Primary Examiner*—Allen C. Ho
(74) *Attorney, Agent, or Firm*—Ziolkowski Patent Solutions Group, SC; Michael A. Della Penna; Carl B. Horton

(57) ABSTRACT

The present invention is directed to an apparatus for supplying power to a rotatable x-ray tube for generation of an x-ray beam for acquisition of CT data. The apparatus includes a slip ring to transfer power from a stationary inverter to a rotatable HV tank. The HV tank conditions the transferred power and creates a voltage potential across the x-ray tube for x-ray generation. The inverter has a single or pair of series resonant circuits connected either directly to the slip ring or indirectly through a transformer to limit frequency content and reduce common-mode component of the voltage and current waveforms carried by the slip ring as well as reduce power losses.

22 Claims, 5 Drawing Sheets

X-RAY GENERATOR AND SLIP RING FOR A CT SYSTEM

BACKGROUND OF INVENTION

The present invention relates generally to diagnostic imaging systems using computed tomography and, more particularly, to an x-ray generator and slip ring for a CT system such that a stationary inverter supplies power to the slip ring for transference to a rotating high voltage tank for creating a voltage potential across a rotating x-ray tube.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

The x-ray generator of a CT system is located within the gantry and, as such, rotates around an imaging bore during data acquisition. The x-ray generation generally includes an x-ray tube, data acquisition system, and arcuate shaped detector arrays. This well-known configuration is shown in FIG. 1. As illustrated, the x-ray generator and slip ring configuration 2 includes an x-ray tube 3, a high voltage (HV) tank 4, and inverter 5 operationally connected to a slip ring 6. Tube 3, HV tank 4, and inverter are each connected and secured to a rotating base 7 that supports each during rotation of the gantry. External to the rotating base 7 and electrically connected to slip ring 6 is a power distribution unit (PDU) 8 that is stationary and therefore does not rotate with tube 3, tank 4, and inverter 5. Inverter 5 is typically fed with a DC voltage, for example, 650 VDC, and generates an AC voltage waveform, for example, approximately 300 VAC, at a specified frequency, e.g. 20 k–50 kHz. The AC voltage is then fed to the HV tank 4 which has a transformer and rectifiers (not shown) that develop a DC HV potential. The HV potential is then applied to the x-ray tube 3. Since the HV tank and inverter are positioned on the rotating base, the power to the inverter is easily transferred to the rotating side across relatively low voltage (~650 VDC) slip ring 6. Rotating base 7 is also designed with one or more auxiliary devices that may include auxiliary power devices, generally referenced 4a.

With this configuration, the inverter 5 is positioned on the rotating base 7 and therefore rotates during data acquisition. A circuit schematic of the inverter is shown in FIG. 2. The inverter 5 includes a number of power switches 9 (e.g. IGBTs) arranged in an H-configuration. Connected to one output of the H-configuration is an LC circuit forming a resonant circuit 10. The output of the resonant circuit 10 and the other output of H-configuration 9 is fed to HV tank 4. The HV tank includes a transformer 11 connected to a rectifier and filter circuit 12 to create a voltage potential across monopolar x-ray tube 3. Inverter 5, HV tank 4, and tube 3 are positioned on the rotating side of slip ring 6. As such, with this known configuration, a relatively low DC voltage is supplied to the slip ring 6 which is then transferred to inverter 5 for conditioning.

This placement of the inverter on the rotating side of the slip ring has a number of drawbacks. For example, rotating at higher gantry speeds is problematic because the mass of the components on the rotating side as well as their associated rotational forces limit gantry speed. Additionally, if gantry speed is increased, the power requirements of the x-ray generator also increase so as to maintain a constant SNR. As such, the size and mass of the x-ray generator components must also be increased to provide the required power. Further, the size of the x-ray generator components in current CT systems have resulted in a cantilevered configuration out from the rotating base. This cantilevered configuration adds a torque on mounting brackets used to secure the components as well as increases the forces placed on the retaining brackets. All of which limit gantry rotational speed.

Therefore, it would be desirable to design an x-ray generator architecture that reduces the size and weight constraints on the rotating base of a CT system thereby allowing for an increase in gantry rotation speed without a deprivation in power delivery to the x-ray tube.

BRIEF DESCRIPTION OF INVENTION

The present invention is a directed to an apparatus for supplying power to an x-ray tube for generation of an x-ray beam for CT data acquisition that overcomes the aforementioned drawbacks. The apparatus includes a slip ring designed to transfer power from a stationary inverter to a rotatable HV tank. The HV tank is designed to condition the transferred power and create a voltage potential across the x-ray tube for x-ray generation. Further, the inverter is constructed to have a single series resonant circuit or a pair of series resonant circuits connected either directly to the slip ring or indirectly through a transformer.

Therefore, in accordance with one aspect of the present invention, an x-ray generator for a CT scanner includes a slip ring to transfer power to a rotating high voltage tank and a rotatable x-ray tube operationally connected to the slip ring to receive power from the high voltage tank. The x-ray tube is configured to project x-rays toward a subject to be scanned positioned in a scanning bay. The x-ray generator also includes a stationary inverter to provide AC power to the slip ring for transference to the high voltage tank.

In accordance with another aspect of the present invention, a CT imager includes a rotatable gantry having an imaging bore disposed therethrough, and a stationary base supporting the gantry. A slip ring is disposed in the rotatable gantry and electrically connected to an x-ray tube and a high voltage tank. The high voltage tank is designed to apply a high voltage potential to the x-ray tube for generation of x-rays for data acquisition. The CT imager also includes a power conditioner external to the gantry to receive a DC voltage and generate an AC voltage waveform that is applied to the high voltage tank through the slip ring.

According to another aspect of the present invention, a CT scanner includes an x-ray tube and a high voltage tank. The high voltage tank is configured to apply a high voltage potential to the x-ray tube. The CT scanner also includes a slip ring to transfer current to the high voltage tank. A stationary base having an inverter to supply AC power to the slip ring for transference to the high voltage tank is also disclosed. The inverter includes at least one resonant circuit that is connected to the slip ring.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

Figure 3:
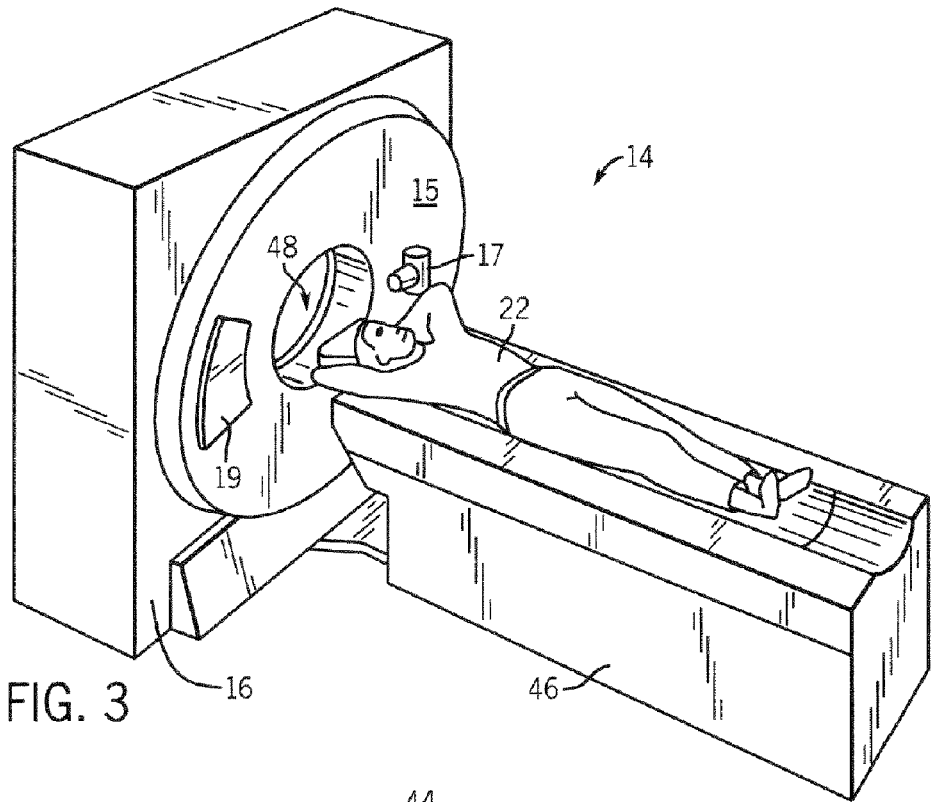
FIG. 3 is a pictorial view of a CT system in accordance with one embodiment of the present invention.
Figure 4:
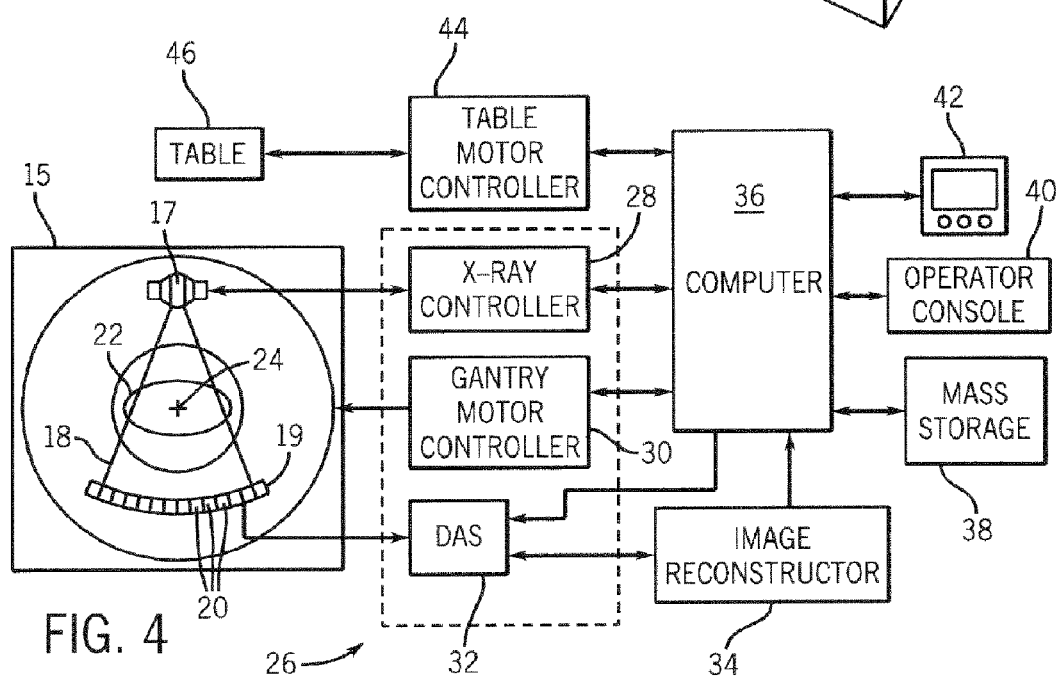
FIG. 4 is a block schematic diagram of the system illustrated in FIG. 1.

Referring to FIGS. 3 and 4, a computed tomography (CT) imaging system 14 is shown as including a rotatable gantry 15 representative of a "third generation" CT scanner. Gantry 15 is positioned in a gantry support 16 and has an x-ray tube 17 that projects a beam of x-rays 18 toward a detector array 19 on the opposite side of the gantry 15. Gantry 15 is designed to rotate and, as such, is defined as a rotating side whereas support 16 does not rotate and, as such, is defined as a stationary side. A slip ring (not shown) is positioned proximate to a rotating base (not shown) for transference of current to x-ray generator components that rotate during data acquisition. The rotating base is designed to support x-ray tube 17, a high voltage (HV) tank (not shown), and other auxiliary components (not shown) during rotation around a medical patient 22. As will be described in greater detail below, the slip ring is constructed to transfer power received from a stationary inverter (not shown) in the gantry support or base to the HV tank so that a voltage potential can be applied to the x-ray tube 17. One skilled in the art will appreciate that the present invention is also applicable to the projection and detection of gamma rays and other HF electromagnetic energy.

Detector array 19 is formed by a plurality of detectors 20 which together sense the projected x-rays that pass through the medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 15 and the operation of x-ray source 17 are governed by a control mechanism 26 of CT system 14. Control mechanism 26 includes an x-ray controller 28 that provides power and timing signals to an x-ray source 17 and a gantry motor controller 30 that controls the rotational speed and position of gantry 15. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 15. Particularly, table 46 moves portions of patient 22 through a gantry opening 48.

Figure 5:
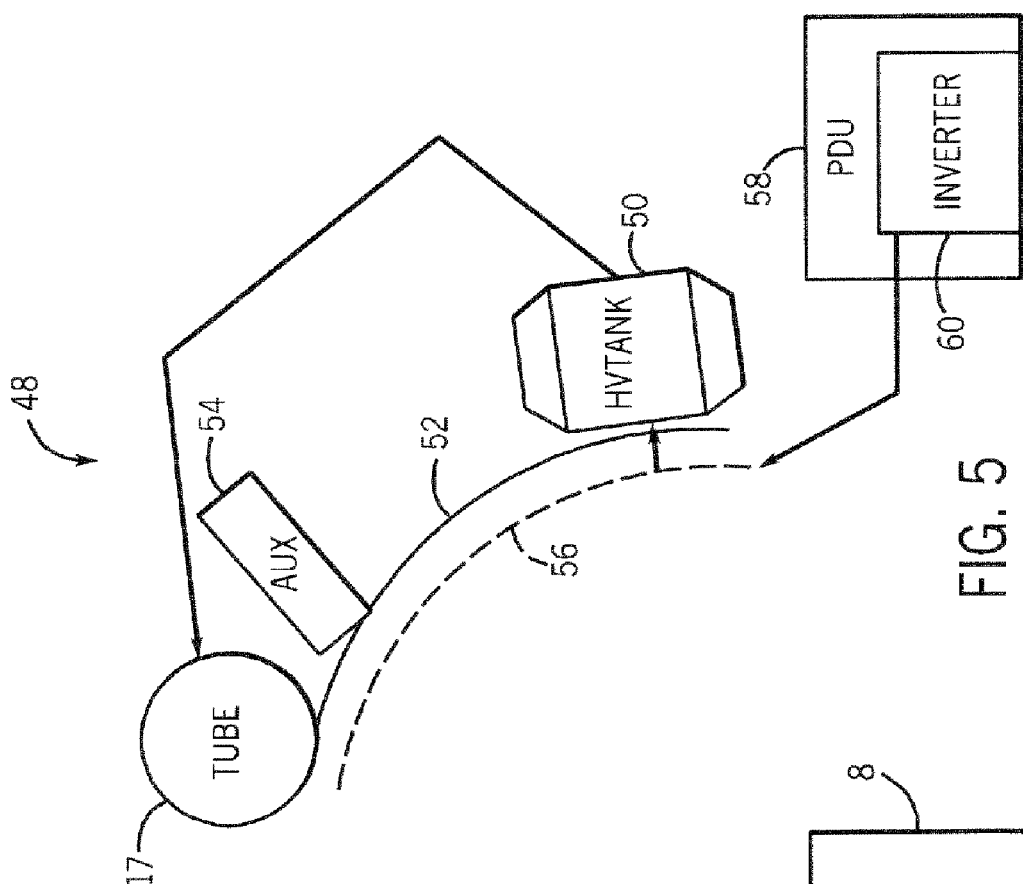
FIG. 5 is a schematic of an x-ray generator and slip ring configuration in accordance with one embodiment of the present invention.
Figure 1:
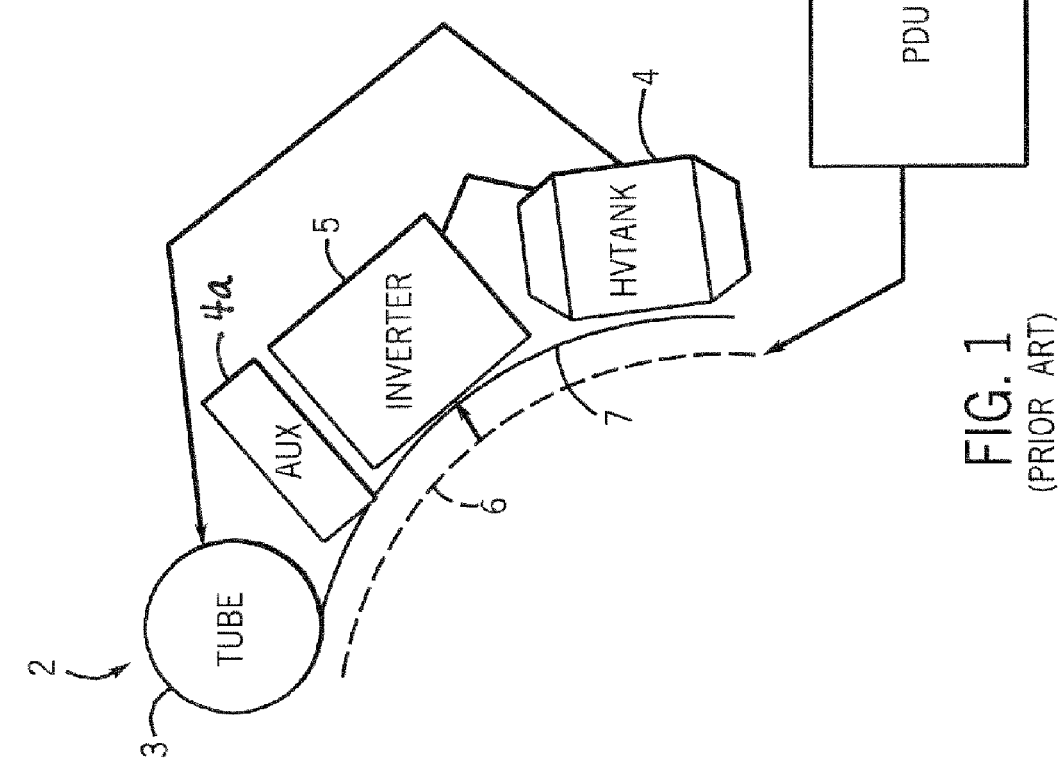
FIG. 1 is a schematic of a known x-ray generator and slip ring configuration for a CT imaging system.
Figure 2:
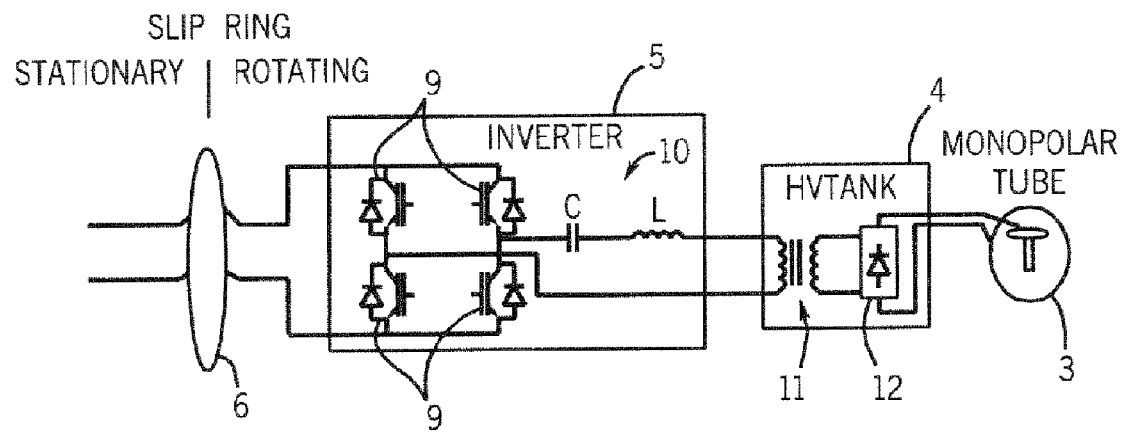
FIG. 2 is circuit schematic of a known inverter topology for use with the configuration shown in FIG. 1.

Referring now to FIG. 5, an x-ray generator and slip ring configuration in accordance with the present invention is shown. The x-ray generator and slip ring configuration 48 includes x-ray tube 17 and high voltage tank connected to a rotating base 52. Rotating base 52 is disposed within the gantry of the CT system and is designed to support rotational movement of the x-ray tube 17 and the high voltage (HV) tank 50. Also supported by rotating base 52 is an auxiliary device 54. HV tank 50 is designed to transform an AC signal to generate a high voltage DC voltage that may be applied to x-ray tube 17. For example, in one embodiment, HV tank 50 is designed to generate up to 160 kV of potential for application to the x-ray tube 17. The x-ray tube generates x-rays for projection toward a patient being scanned as a function of the voltage placed thereacross.

Configuration 48 also includes a slip ring that is schematically represented by arc 56 that is generally annular in shape and is designed to transfer electric current to HV tank 50. In this regard, slip ring 56 is designed to receive an AC voltage waveform from power distribution unit (PDU) 58. As illustrated, PDU 58 may include an inverter 60 designed to supply the AC waveform to slip ring 56. One skilled in the art will appreciate, however, that the inverter may be positioned external to the PDU. Additionally, as will be discussed in greater detail below, inverter 60 is stationary relative to the rotational components of configuration 48 and thus does not rotate around the patient during data acquisition. Moreover, in one embodiment, inverter 60 is designed to supply a ~300V AC waveform at a frequency of 30 kHz to slip ring 56. One skilled in the art will appreciate that other frequency ranges are contemplated such as approximately 20 k to 1 MHz.

Figure 6:
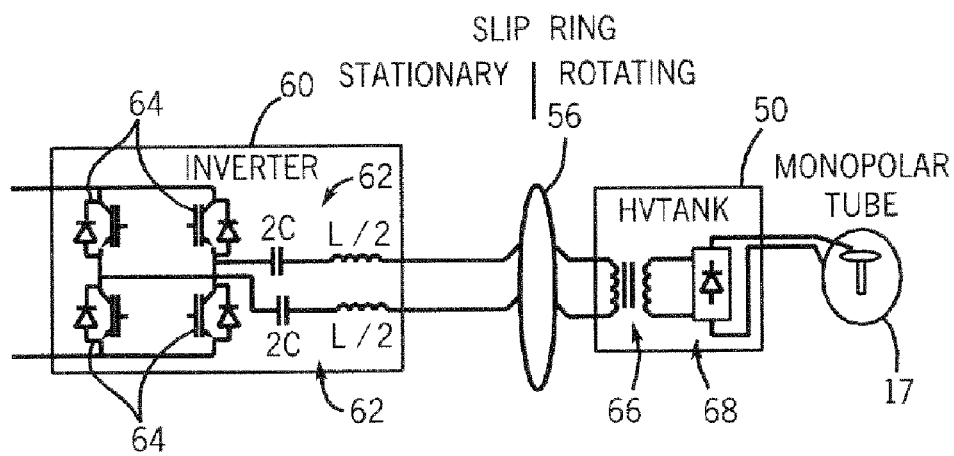
FIG. 6 is a circuit schematic of an inverter topology for the configuration shown in FIG. 5 in accordance with another embodiment of the present invention.

Slip ring 56 has a relatively large diameter and therefore can behave as a radiating antenna. Therefore, in order to minimize electromagnetic radiation, it is imperative to limit frequency content of the current and voltage waveforms on the slip ring. To this end, as shown in FIG. 6, the present invention includes an inverter topology to limit frequency content of the waveforms transferred on the slip ring. Inverter 60 includes a pair of resonant circuits 62. Each resonant circuit includes a series connected capacitor, C, and inductor, L. Each resonant circuit 62 is connected to an output of a plurality of power switches 64 arranged in an H-configuration. The power switches may include MOSFETs, IGBTs, and the like. The power switches 64 are designed to receive a high voltage DC input, such as 650 V DC, and generate an AC voltage at a variable frequency, i.e. approximately 20–100 RFTz.

The resonant circuits are connected to the outputs of the power switch configuration and thus are positioned between the power switch outputs and slip ring 56. It should be noted that, in one embodiment, the values of the inductive and reactive components of the resonant circuits are the same for each converter. The resonant circuits are designed to smooth out the fast transitions of the power switches thereby limiting the frequency content and reducing the common mode component of the waveforms transferred to slip ring 56.

Still referring to FIG. 6, slip ring 56 defines a boundary between a stationary side and a rotating side of the x-ray generator. As noted above, the inverter and its associated topology is positioned on the stationary side of slip ring 56. As such, the inverter does not rotate with high voltage tank 50 or x-ray tube 17 during the data acquisition process. The rotating side of the x-ray generator and slip ring configuration includes HV tank 50 which is designed to receive an AC waveform from slip ring 56 and condition the waveform to provide a high voltage DC potential to x-ray tube 17. HV tank 50 includes a transformer 66 and a rectifier and filter circuit 68 to condition the AC voltage signal transferred by slip ring 56. In one exemplary embodiment, HV tank 50 is designed to apply a 160 kV DC potential across x-ray tube 17.

Figure 7:
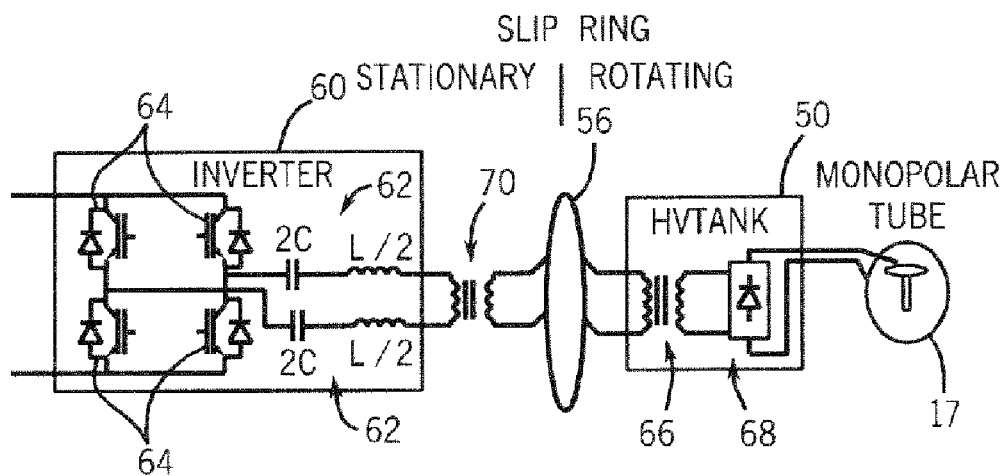
FIG. 7 is a circuit schematic of an alternate inverter topology for the configuration shown in FIG. 5 in accordance with yet another embodiment of the present invention.

Referring now to FIG. 7, an inverter topology in accordance with another embodiment of the present invention is shown. Inverter 60, in this embodiment, is similar to the topology described with respect to FIG. 6, and includes a number of power switches arranged in an H-configuration designed to output an AC voltage waveform that is smoothed by a pair of series resonant circuits 62. However, in contrast to the topology illustrated in FIG. 6, the configuration shown in FIG. 7 includes a transformer positioned between the resonant circuit outputs and the slip ring 56. Transformer 70 is introduced into the configuration to control the effective inductance of slip ring 56. For example, slip ring 56 has an inductance that typically ranges from 0.2 mH to 0.6 mH, depending upon its rotational position. By adding transformer 70 into the circuit, the effective inductance is reduced by $N^2$, wherein N is the turns ratio of transformer 70. For example, if the turns ratio of transformer 70 is 1:N, then the inductance or variation of slip ring 56 is reduced by a factor of 25, from 0.4 mH to 0.016 mH, for instance. Furthermore, the slip ring has a series resistance that is also reduced by $N^2$ thereby reducing losses.

Incorporating transformer 70 at a turns ratio of 1:N into the x-ray generator and slip ring configuration requires that the turns ratio of transformer 66 and HV tank 50 be reduced by N to compensate for the incorporation of transformer 70. That is, the turns ratio of transformer 66 would be 1:X–N where N is the turns ratio of transformer 70 and X is the turns ratio of transformer 66 without transformer 70 being in the system. For example, if transformer 66 would otherwise have a turns ratio of 8 absent transformer 70, then the incorporation of transformer 70 with a turns ratio of 5 would require that transformer 66 be configured to have a turns ratio of 3. Additionally, the slip ring has an effective inductance of $Y/N^2$ where Y equals the inductance of the slip ring without transformer 70 being included in the circuit topology.

With the heretofore described invention whereupon the inverter assembly and its associated bracket are removed from the rotating side, there may be a counter-balance typically associated with the CT system that can now be removed that is equal in mass to the inverter assembly. Repositioning of the inverter in the stationary side of the system as well as removal of any counter-balance may allow for elimination of any cantilevered configuration and thus provides a more uniformly balanced gantry which is critical for higher gantry speeds such as 0.2 seconds per revolution. Additionally, the high frequency AC waveform at the slip ring may allow for a contactless slip ring thereby eliminating slip ring brushes. Further, by repositioning the inverter from the rotating side to the stationary side of the system, room is now available for increased generator size for generation of higher power levels, such as 150 kW and 200 kW, typically needed for faster scanning.

Figure 8:
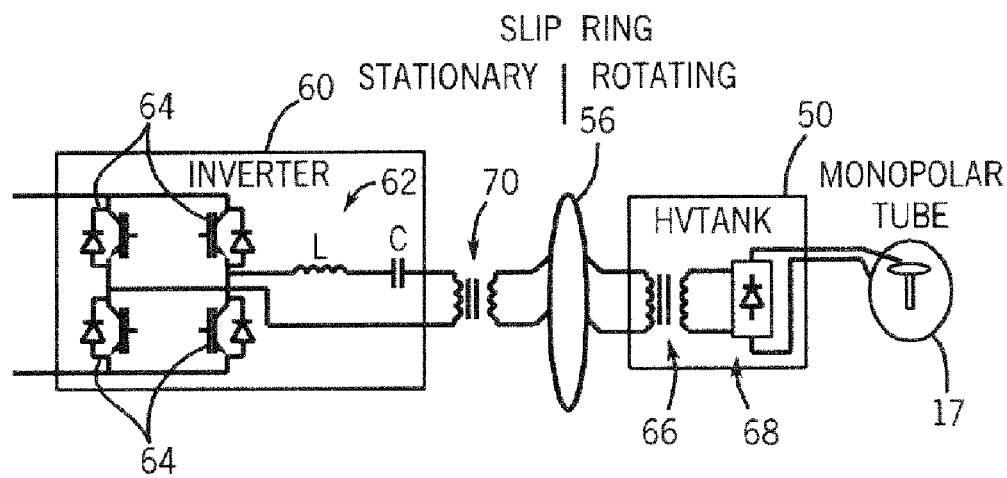
FIG. 8 is a circuit schematic of another inverter topology for the configuration shown in FIG. 5 in accordance with another embodiment of the present invention.

Referring now to FIG. 8, an x-ray generator and slip ring configuration in accordance with another embodiment of the invention is shown. The configuration of FIG. 8 is similar to the embodiment of FIG. 7; however, the configuration of FIG. 8 utilizes only a single series resonant circuit 62. In this regard, one output of the H-configuration of power switches 64 is fed to resonant circuit 62 and the other output is directly connected to transformer 70. The output of resonant converter 62 is also fed to transformer 70. As such, the positive portion of the AC waveform output by the power switches is fed to resonant circuit for smoothing whereas the negative portion of the AC waveform is fed directly to transformer 70. Similar to the embodiments of FIGS. 6 and 7, the inverter 60 is stationary whereas HV tank 50 and x-ray tube 17 rotate. Current passed to the slip ring 56 by transformer 70 is transferred to HV tank 50 for generation of a high voltage potential that is applied across x-ray tube 17 for generation of x-rays for CT data acquisition. Similar to the configuration illustrated in FIG. 7, the turns ratio of transformer 70 in FIG. 8 impacts the turns ratio of transformer 66 of the HV tank 50. Additionally, high frequency and common-mode components on slip ring waveforms are also reduced.

Figure 9:
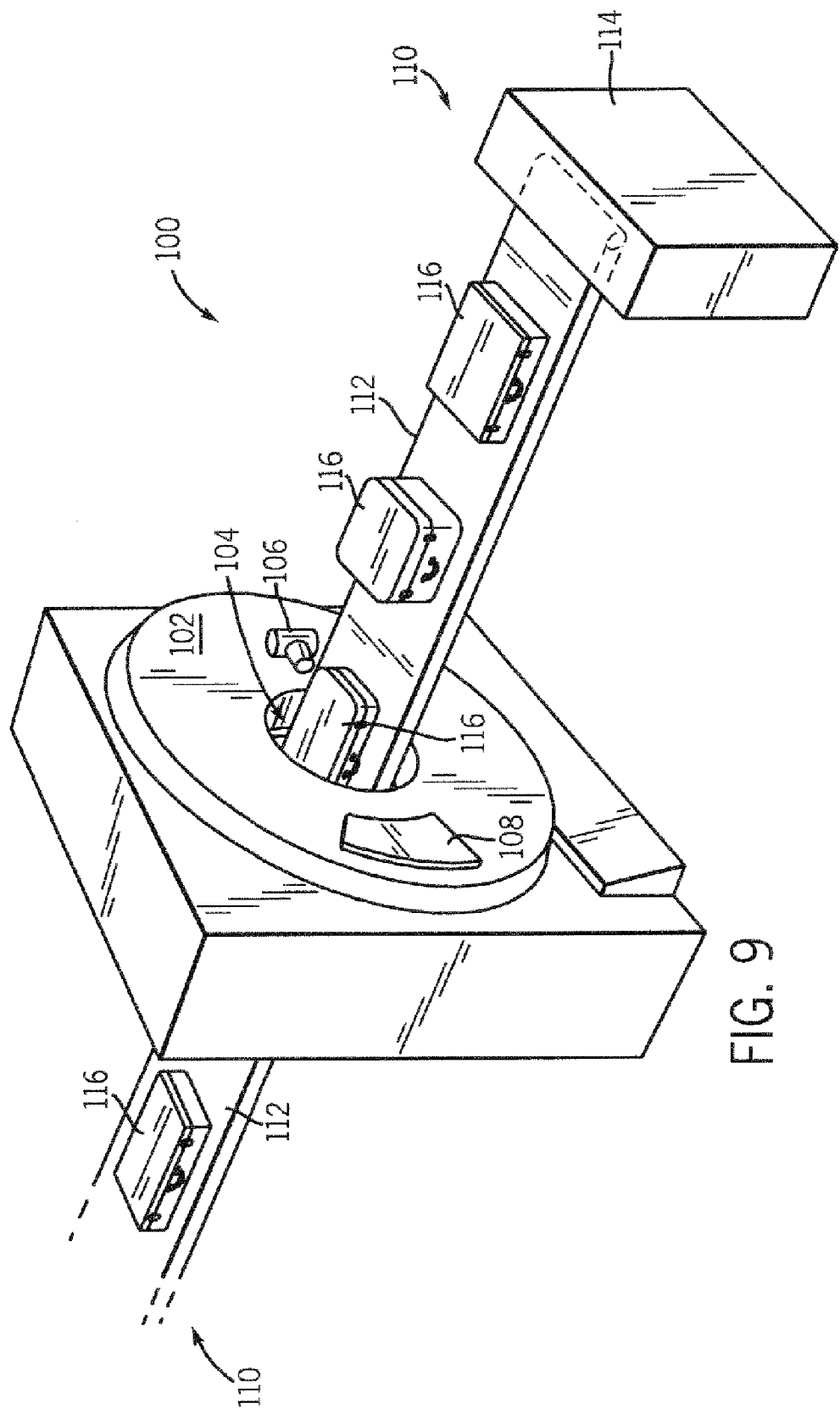
FIG. 9 is a pictorial view of a CT system for use with a non-invasive package inspection system.

Referring now to FIG. 9, package/baggage inspection system 100 incorporating the x-ray generator and slip ring architecture and inventor topology described above includes a rotatable gantry 102 having an opening 104 therein through which packages or pieces of baggage may pass. The rotatable gantry 102 houses a high frequency electromagnetic energy source 106 as well as a detector assembly 108. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

Therefore, in accordance with one embodiment of the present invention, an x-ray generator for a CT scanner includes a slip ring to transfer power to a rotating high voltage tank and a rotatable x-ray tube electrically connected to the slip ring to receive power from the high voltage tank. The x-ray tube is configured to project x-rays toward a subject to be scanned positioned in a scanning bay. The x-ray generator also includes a stationary inverter to provide AC power to the slip ring for transference to the high voltage tank.

In accordance with another embodiment of the present invention, a CT imager includes a rotatable gantry having an imaging bore disposed therethrough, and a stationary base supporting the gantry. A slip ring is disposed in the rotatable gantry and electrically connected to an x-ray tube and a high voltage tank. The high voltage tank is designed to apply a high voltage potential to the x-ray tube for generation of x-rays for data acquisition. The CT imager also includes a power conditioner external to the gantry to receive a DC voltage and generate an AC voltage waveform that is applied to the high voltage tank through the slip ring.

According to another embodiment of the present invention, a CT scanner includes an x-ray tube and a high voltage tank. The high voltage tank is configured to apply a high voltage potential to the x-ray tube. The CT scanner also includes a slip ring to transfer current to the high voltage tank. A stationary base having an inverter to supply AC power to the slip ring for transference to the high voltage tank is also disclosed. The inverter includes a single or pair of resonant circuits that are connected to the slip ring either directly or through a transformer.

The present invention has been described in terms of the preferred embodiment, and it is recognized that equivalents, alternatives, and modifications, aside from those expressly stated, are possible and within the scope of the appending claims.

What is claimed is:

1. An x-ray generator for a CT scanner, the generator comprising:
   a slip ring to transfer power to a rotating high voltage (HV) tank;
   a rotatable x-ray tube operationally connected to the slip ring to receive power from the HV tank and project x-rays toward a subject to be scanned; and
   a stationary inverter to provide AC power to the slip ring for transference to the HV tank, the stationary inverter having a number of power switches arranged in an H-bridge configuration, the configuration having a pair of outputs such that at least one output is connected to a resonant circuit that is connected to the slip ring.

2. The x-ray generator of claim 1 wherein the resonant circuit is connected to the slip ring.

3. The x-ray generator of claim 2 wherein the resonant circuit includes a capacitor and an inductor connected in series.

4. The x-ray generator of claim 1 wherein the resonant circuit is connected to an input of a transformer and wherein the transformer has outputs connected to the slip ring.

5. The x-ray generator of claim 4 wherein the transformer has a turns ratio of 1:N and a transformer of the high voltage tank has a turns ratio of 1:X–N.

6. The x-ray generator of claim 5 wherein the slip ring has an effective inductance of $Y/N^2$.

7. A CT imager comprising:
   a rotatable gantry having an imaging bore disposed therethrough, and a stationary base supporting the gantry;
   a slip ring disposed in the rotatable gantry and electrically connected to an x-ray tube and a HV tank, the HV tank designed to apply a HV potential to the x-ray tube;
   a power conditioner external to the gantry to receive a DC voltage and generate an AC voltage waveform that is applied to the HV tank through the slip ring, the power conditioner having an inverter connected to a series-resonant circuit that is connected to the slip ring; and
   a transformer connected between the series-resonant circuit and the slip ring.

8. The CT imager of claim 7 further comprising a power distribution unit (PDU) disposed in the stationary base and wherein the power conditioner is disposed in the PDU.

9. The CT imager of claim 7 wherein the power conditioner is positioned in the stationary base.

10. The CT imager of claim 7 wherein the inverter is configured to supply an approximate 20 k–1 MHz AC waveform to the slip ring.

11. The CT imager of claim 10 wherein the HV tank is configured to receive the AC waveform from the slip ring and transform the AC waveform to generate up to approximately 160 kV therefrom.

12. The CT imager of claim 7 wherein the at least one resonant circuit is configured to limit frequency content of current and voltage waveforms on the slip ring.

13. The CT imager of claim 7 wherein the transformer has a turns ratio of 1:N and wherein a transformer of the high voltage tank has a turns ratio of 1:X–N.

14. The CT imager of claim 13 wherein the slip ring has an effective inductance of $Y/N^2$.

15. A CT scanner comprising:
    a rotatable x-ray tube and a rotatable HV tank, the HV tank configured to apply a high voltage potential to the x-ray tube;
    a slip ring to transfer current to the HV tank;
    a stationary base having an inverter to supply AC power to the slip ring for transference to the HV tank;
    the inverter having at least one resonant circuit connected to the slip ring; and
    wherein the at least one resonant circuit includes a pair of resonant circuits.

16. The CT scanner of claim 15 further comprising a transformer connected to the at least one resonant circuit and the slip ring.

17. The CT scanner of claim 15 having a gantry rotatable at a speed of approximately 0.1 to 0.3 seconds per revolution.

18. The CT scanner of claim 15 wherein the inverter is designed to supply 300 VAC.

19. The CT scanner of claim 15 further comprising a power distribution unit having the inverter disposed therein.

20. The CT scanner of claim 15 incorporated into one of a medical imaging machine and a parcel inspection apparatus.

21. A CT imager comprising:
    a rotatable gantry having an imaging bore disposed therethrough, and a stationary base supporting the gantry;
    a slip ring disposed in the rotatable gantry and electrically connected to an x-ray tube and a HV tank, the HV tank designed to apply a HV potential to the x-ray tube;
    a power conditioner external to the gantry to receive a DC voltage and generate an AC voltage waveform that is applied to the HV tank through the slip ring, the power conditioner having an inverter connected to a series-resonant circuit that is connected to the slip ring; and
    wherein the inverter is configured to supply an approximate 20 k–1 MHz AC waveform to the slip ring.

22. The CT imager of claim 21 wherein the HV tank is configured to receive the AC waveform from the slip ring and transform the AC waveform to generate up to approximately 160 kV therefrom.

* * * * *

UNITED STATES PATENT AND TRADEMARK OFFICE
CERTIFICATE OF CORRECTION

PATENT NO. : 6,975,698 B2  
DATED : December 13, 2005  
INVENTOR(S) : Katcha et al.

Page 1 of 1

It is certified that error appears in the above-identified patent and that said Letters Patent is hereby corrected as shown below:

<u>Column 8,</u>  
Line 9, delete "20 k--1" and substitute -- 20k-1 --.  
Line 59, delete "20 k-1" and substitute -- 20k-1 --.

Signed and Sealed this

Fourth Day of April, 2006

JON W. DUDAS  
*Director of the United States Patent and Trademark Office*